US006417399B1

(12) United States Patent
Bialer et al.

(10) Patent No.: US 6,417,399 B1
(45) Date of Patent: *Jul. 9, 2002

(54) AMELIORATION OF NEUROLOGICAL DISORDERS BY THE ADMINISTRATION OF (2R),(3S), AND/OR (2S),3(S) STEREOISOMERS OF VALNOCTAMIDE

(75) Inventors: Meir Bialer; Boris Yagen, both of Jerusalem; Ofer Spiegelstein, Mevasseret Zion, all of (IL); Michael Roeder, Gomaringen; Volker Schurig, Tubingen, both of (DE)

(73) Assignee: Yissum Research Development Company of the Hebrew University of Jerusalem, Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,240

(22) PCT Filed: Jan. 14, 1998

(86) PCT No.: PCT/IL98/00015

§ 371 (c)(1),
(2), (4) Date: Jul. 13, 1999

(87) PCT Pub. No.: WO98/30536

PCT Pub. Date: Jul. 16, 1998

(30) Foreign Application Priority Data

Jan. 14, 1997 (IL) .................................................. 120006

(51) Int. Cl.[7] ........................ C07C 231/18; A61K 31/16

(52) U.S. Cl. ........................ 564/216; 564/215; 564/134; 564/142; 564/143; 514/629; 514/923

(58) Field of Search ................................. 514/629, 923; 564/215, 216, 134, 142, 143

(56) References Cited

U.S. PATENT DOCUMENTS

| 3,056,726 A | | 10/1962 | Marsh | |
|---|---|---|---|---|
| 5,387,338 A | * | 2/1995 | Pirkle et al. | .............. 210/198.2 |
| 5,491,266 A | * | 2/1996 | Babin et al. | ................. 568/449 |
| 5,506,268 A | * | 4/1996 | Balandrin et al. | .......... 514/629 |

OTHER PUBLICATIONS (1) Bialer, M. et al., "Pharmacokinetics of a Valpromide Isomer, Valnoctamide, in Healthy Subjects", Eur. J. Clin. Pharmacol., (1990), 38(3), pp. 289–291.
(2) J. P. Chambon et al., "Valnoctamide: Pharmacological Data Suggesting an Antiepileptic Activity", Neurosci. Lett. Suppl., vol. 5, 1980, p. S327.
(3) Barel, Shimon et al., "Stereoselective Pharmacokinetic Analysis of Valnoctamide in Healthy Subjects and in Patients with Epilepsy", Clin. Pharmacol. Ther. (St. Louis) (1997), 61(4), pp. 442–449.
(4) Pisani, F. et al., "Carbamazepine–Valnoctamide Interaction in Epileptic Patients: In Vitro/in Vivo Correlation", Epilepsia (N.Y.) (1993), 34(5), pp. 954–959.

* cited by examiner

*Primary Examiner*—Shailendra Kumar
(74) *Attorney, Agent, or Firm*—Lowe Hauptman Gilman & Berner, LLP (57) ABSTRACT

The present invention generally relates to the individual stereoisomers of the drug valnoctamide (a mixture of four stereoisomer kinds, VCD-valmethamide or 2-ethyl-3-methyl pentanamide) useful in treatment of neurological and psychotic disorders such as different kinds of epilepsy and affective disorders, and useful as tranquilizers and to treat pain, and to pharmaceutical compositions containing, as an active ingredient, these stereoisomers. The present invention further relates to a method for stereoselective separation and quantification of the four stereoisomers from a racemic mixture of VCD or plasma of patients treated with the racemic drug. The present invention further relates to a unique method for the synthesis of the individual stereoisomers.

24 Claims, 9 Drawing Sheets

AMELIORATION OF NEUROLOGICAL DISORDERS BY THE ADMINISTRATION OF (2R),(3S), AND/OR (2S),3(S) STEREOISOMERS OF VALNOCTAMIDE

This application is a 371 of PCT/IL98/000/5, filed Jan. 14, 1998.

FIELD OF THE INVENTION

The present invention generally relates to the individual stereoisomers of the drug valnoctamide (a mixture of four stereoisomer kinds, VCD-valmethamide or 2-ethyl-3-methyl pentanamide) useful in treatment of neurological and psychotic disorders such as different kinds of epilepsy and affective disorders, and useful as tranquilizers and to treat pain, and to pharmaceutical compositions containing, as an active ingredient, these stereoisomers. The present invention further relates to a method for stereoselective separation and quantification of the four stereoisomers from a racemic mixture of VCD or plasma of patients treated with the racemic drug.

The present invention further relates to a unique method for the synthesis of the individual stereoisomers.

BACKGROUND OF THE INVENTION

Epilepsy is an ancient disease which affects about 1% of the global population. Despite the progress in antiepileptic therapy, about 25% of the epileptic patients continue to suffer from uncontrolled seizures and medication toxicity. At present, there are four major epileptic drugs in use: phenobarbital, phenytoin, carbamazepine and valproic acid. Valproic acid (VPA) is one of the major antiepileptic drugs. It has two major side effects, teratogenicity and hepatotoxicity, which have been associated with valproate therapy. Valnoctamide (VCD-valmethamide or 2-ethyl-3-methyl pentanamide) is an isomer of valpromide (VPD) and is sold as an over- the-counter drug in several European countries. It has been available clinically for many decades and is still used as a mild tranquilizer and occasionally as an antiepileptic drug (Chambon JP, Perio A, Neurosci. Lett [Suppl]5: S327-S327, 1980). Valpromide (VPD) is used as an anticonvulsant and antipsychotic agent, and in humans it is a prodrug of valproic acid (VPA). VPD may also be useful in treatment of neurological disorders and psychotic or affective disorders such as convulsions and epilepsy, and useful as tranquilizers and to treat pain. Recently, interest in VCD was revived by the observation that this compound possesses marked anticonvulsant activity in animal models. Both VCD and VPD are three times more potent as anticonvulsants than VPA. In addition, VPD, unlike VPA, has not been found to be teratogenic in animals possibly because it contains a carboxamide moiety instead of a carboxylic acid. However, in humans VPD acts as a prodrug to VPA and therefore its superiority over VPA in animal models does not have clinical implications. Unlike VPD, VCD acts as a drug on its own in both animals and humans and undergoes only slow and very little transformation to its corresponding (less active) valnoctic acid (VCA). Based on its anticonvulsant potency, metabolic stability and lack of teratogenicity, VCD was viewed as having potential to become a new antiepileptic drug. It was recently found, however, that VCD is an inhibitor of the enzyme epoxide hydrolase. This inhibition was regarded as a drawback to the development of racemic VCD as a new antiepileptic drug. In the present invention, for the first time, characterization of the pharmacokinetics (PK) of the four stereoisomers of VCD in humans was performed This characterization clearly demonstrates that VCD pharmacokinetics is stereoselective, with one isomer exhibiting a much higher clearance and a shorter half-life compared with the other stereoisomers. Stereoselective pharmacokinetics has been demonstrated previously with different drugs, such as verapamil and mephenytoin, but this is the first time that PK stereoselectivity has been shown for an amide of an aliphatic short-chain fatty acid.

The present invention relates to the stereoisomers of valnoctamide which are useful in treatment of neurological and psychotic disorders such as different kinds of epilepsy and affective disorders, and useful as tranquilizers and to treat pain. The present invention further relates to a method for stereoselective separation and quantification of the four stereoisomers from a racemic mixture of VCD and to a method for the synthesis of the 2S, 3S and 2R,3S VCD stereoisomers.

The stereoisomers have all of the benefits, and more, of the racemic drug of valnoctamide, but do not have any of its drawbacks, making them preferable for use in the treatment of convulsions and epilepsy and as an active ingredient in pharmaceutical compositions for the treatment of the latter. The present invention further relates to a method for separating the four stereoisomers of racemic valnoctamide. This method is a new stereoselective gas chromatography-mass spectrometry (GC-MS) assay which allows specific and sensitive quantitation of valnoctamide stereoisomers in human plasma. This method is the only one available for investigating the pharmacokinetics and pharmacodynamics of valnoctamide stereoisomers in plasma samples, investigations which may have important practical implications for the development of a new anticonvulsant drug for humans. The present invention further relates to a unique method for the synthesis of the individual stereoisomers.

SUMMARY OF THE INVENTION

The present invention relates to stereoisomers of valnoctamide (one of four isomers of valnoctamide) useful in treatment of neurological and psychotic disorders such as different kinds of epilepsy and affective disorders, and useful as tranquilizers and to treat pain, and to pharmaceutical compositions, containing as an active ingredient stereoisomers or a stereoisomer of valnoctamide, useful as anticonvulsant drugs or tranquilizers.

The present invention further relates to a method for separating valnoctamide isomers comprising subjecting a mixture of racemic valnoctamide to gas chromatography preferably with oven temperature programming conditions; 50° C. for 1 minute, increasing at a rate of 8° C./minute until 100° C., holding for a minute then reaching final temperature of 250° C. at a rate of 4° C./minute; the injector temperature is 240° C. and the GC-MS transfer line temperature is 250° C.; inlet pressure is 5 psi with a linear flow rate 20 cm/second and the GC carrier gas is helium. Following, the isomers are separated on a chiral stationary phase column, preferably consisting of octakis (3-O-butanoyl-2,6-di-o-pentyl)-γ-cyclodextin chemically linked via a 6-mono-octamethylene spacer to a dimethylpolysiloxane and being coated on a fused silica capillary column of 25 m×250 μm coated by 0.25 μm octakis (3-O-butanoyl-2,6-di-o-pentyl)-γ-cyclodextrin.

The present invention further relates to a method of separating valnoctamide isomers comprising subjecting a mixture of racemic valnoctamide to gas chromatography preferably with oven temperature programming conditions; 50° C. for 1 minute, increasing at a rate of 8° C./minute until 100° C., holding for a minute, then reaching final temperature of 250° C. at a rate of 4° C./minute; the injector temperature is 240° C. and the GC-MS transfer line temperature is 250° C.; inlet pressure is 5 psi with a linear flow rate of 20cm/sec and the GC carrier gas is helium. Following, the isomers are separated on a chiral stationary phase column, preferably consisting of octakis (3-O-butanoyl-2,6-di-o- pentyl)-γ-cyclodextrin chemically linked via a 6-mono-octamethylene spacer to a dimethyl polysiloxane and being coated with a fused silica capillary column of 25m X 250 μm coated with 0.25 μm octakis (3-O-butanoyl-2,6-di-o-pentyl)-γ-cyclodextrin.

DETAILED DESCRIPTION OF THE INVENTION

Figure 1:
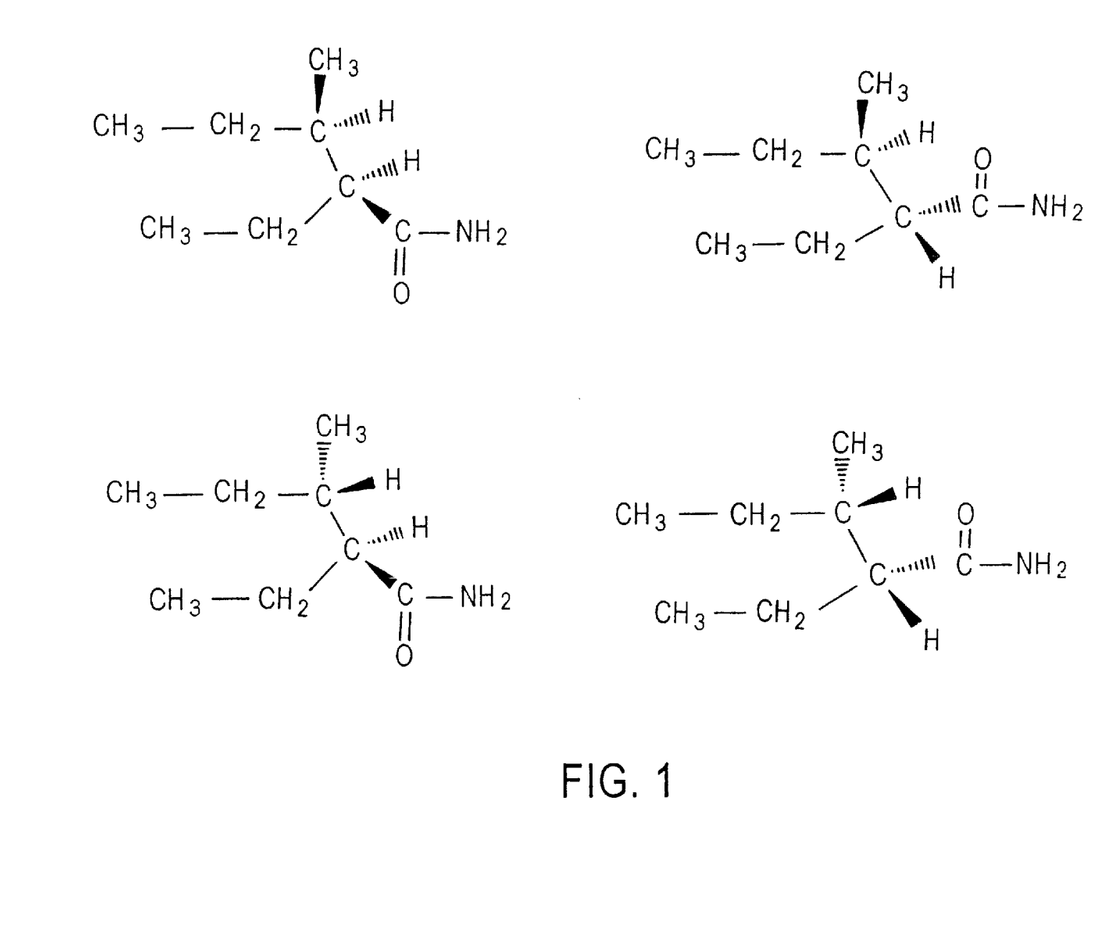

The present invention relates to stereoisomers of the drug, valnoctamide (VCD-valmethamide or 2-ethyl-3-methyl pentanamide), useful in treatment of neurological and psychotic disorders such as different kinds of epilepsy and affective disorders, and useful as tranquilizers and to treat pain, and to pharmaceutical compositions containing, as an active ingredient, these stereoisomers. VCD, as compared with the well-known antiepileptic drug VPA, is retained in the body for a relatively long period and the plasma levels of its corresponding acid (VCA) are much lower than those of the parent drug. In contrast to VPD, which has a high (metabolic) extraction ratio by the liver, where it undergoes extensive first-pass metabolism to its corresponding acid VPA, VCD does not have a high affinity for hepatic metabolism. This is reflected by its low oral clearance and its half-life, which is ten times higher than that of VPD (Bialer et al., Eur. J. Clin. Pharmacol. 38: 289–291, 1990). Based on its anticonvulsant potency, metabolic stability and lack of teratogenicity. VCD was viewed as having potential to become a new antiepileptic drug. However, it was recently found (Pisani et al., Epilepsia 34:954–959, 1993) that VCD is an inhibitor of the enzyme epoxide hydrolase. The inhibition of this enzyme, resulting in the decreased clearance of CBZ-E in patients who were treated with the antiepileptic drug carbamazepine (CBZ) together with VCD, caused in these patients signs suggestive of CBZ intoxication. This inhibition was regarded as a drawback to the development of racemic VCD as a new antiepileptic drug, but since VCD has two chiral centers (as depicted in FIG. 1), and there are two pairs of enantiomers in the VCD molecule, there is, a possibility that its pharmacokinetics (PK) and pharmacodynamics (PD), including toxicological potential and epoxide hydrolase inhibition, are stereoselective. By itself, PK stereoselectivity could lead to PD stereoselectivity, and have considerable implications for the further development of an antiepileptic drug. The method for the stereoselective separation and quantfication of the four stereoisomers from a racemic mixture of VCD or plasma of patients treated with the racemic drug, of the present invention was developed based on this background. This method is a new stereoselective gas chromatography-mass spectrometry (GC-MS) assay which allows the specific and sensitive quantitation of VCD stereoisomers.

Figure 6:
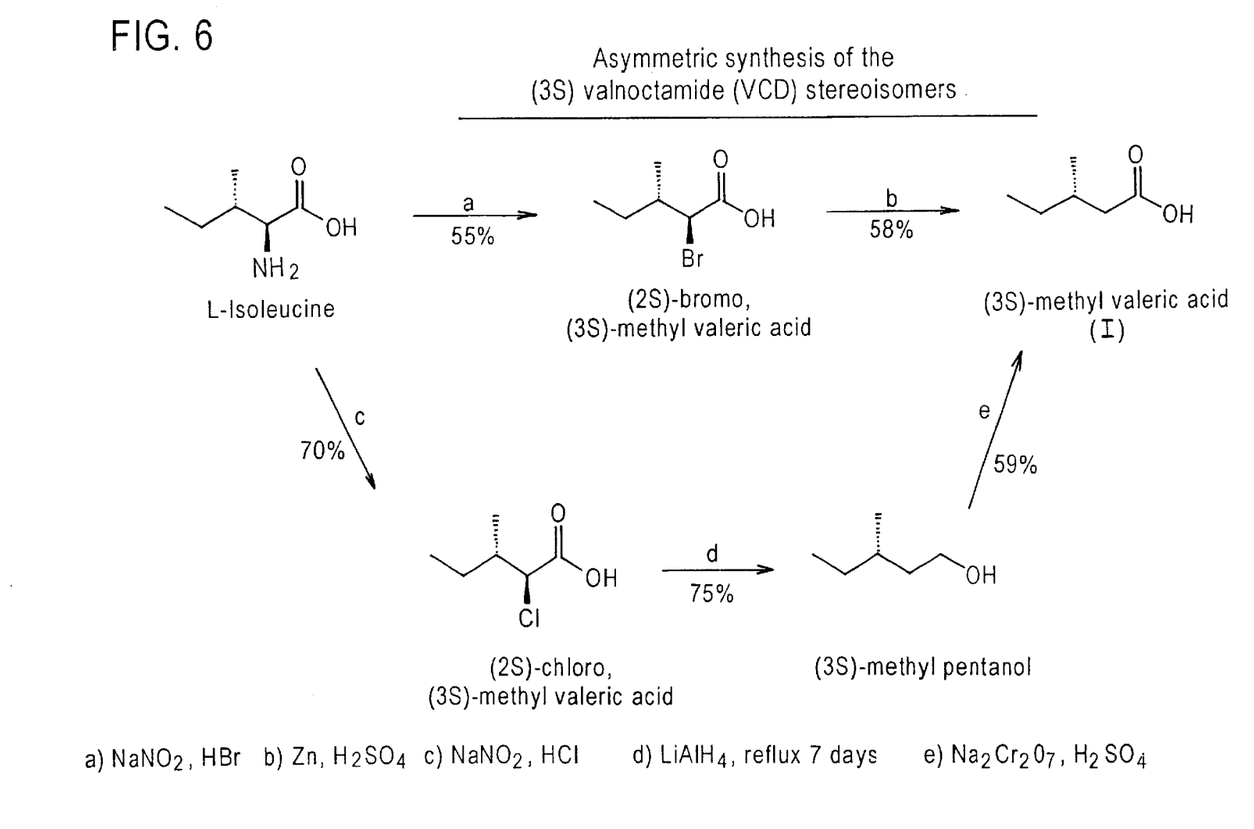
Figure 7:
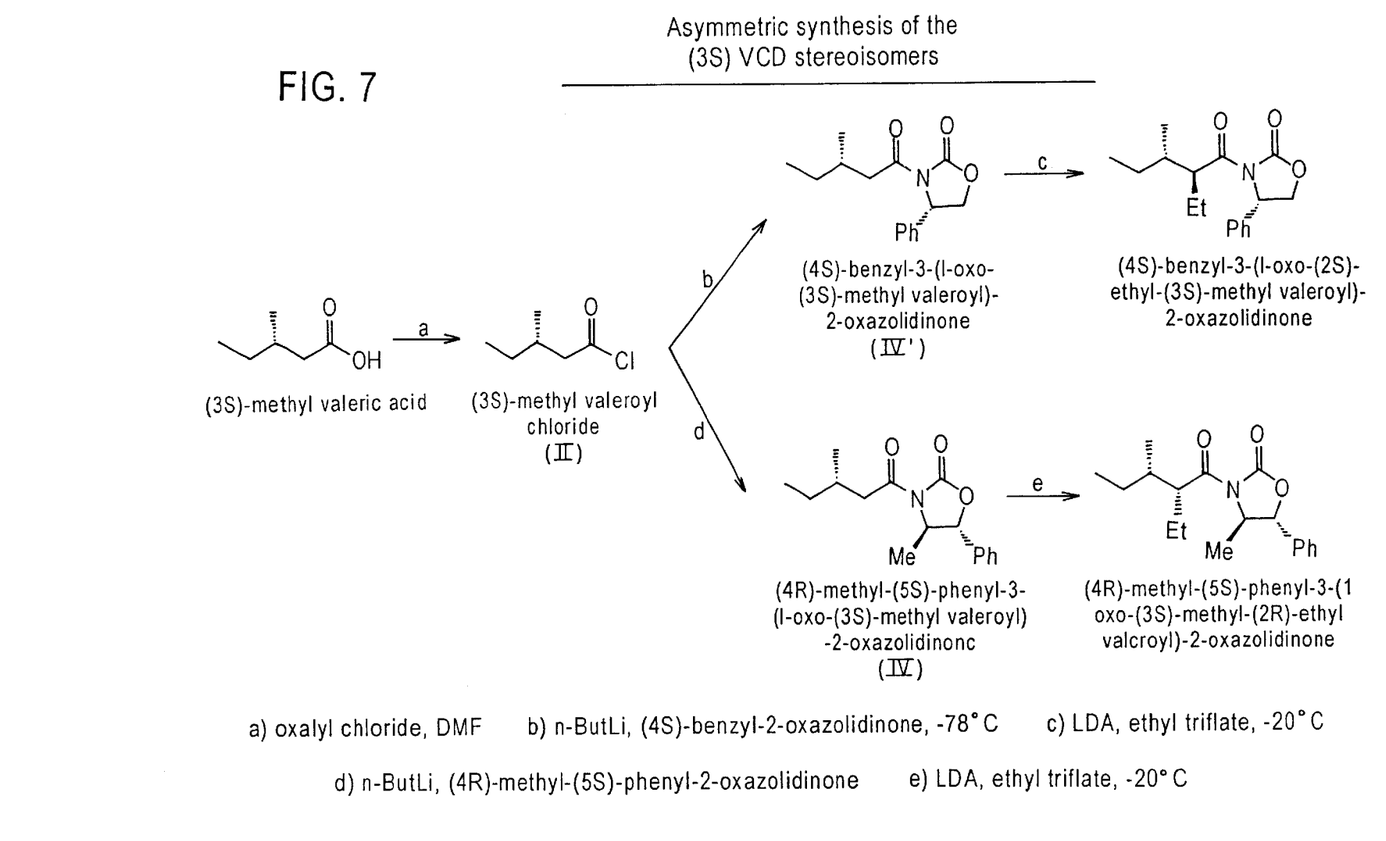
Figure 8:
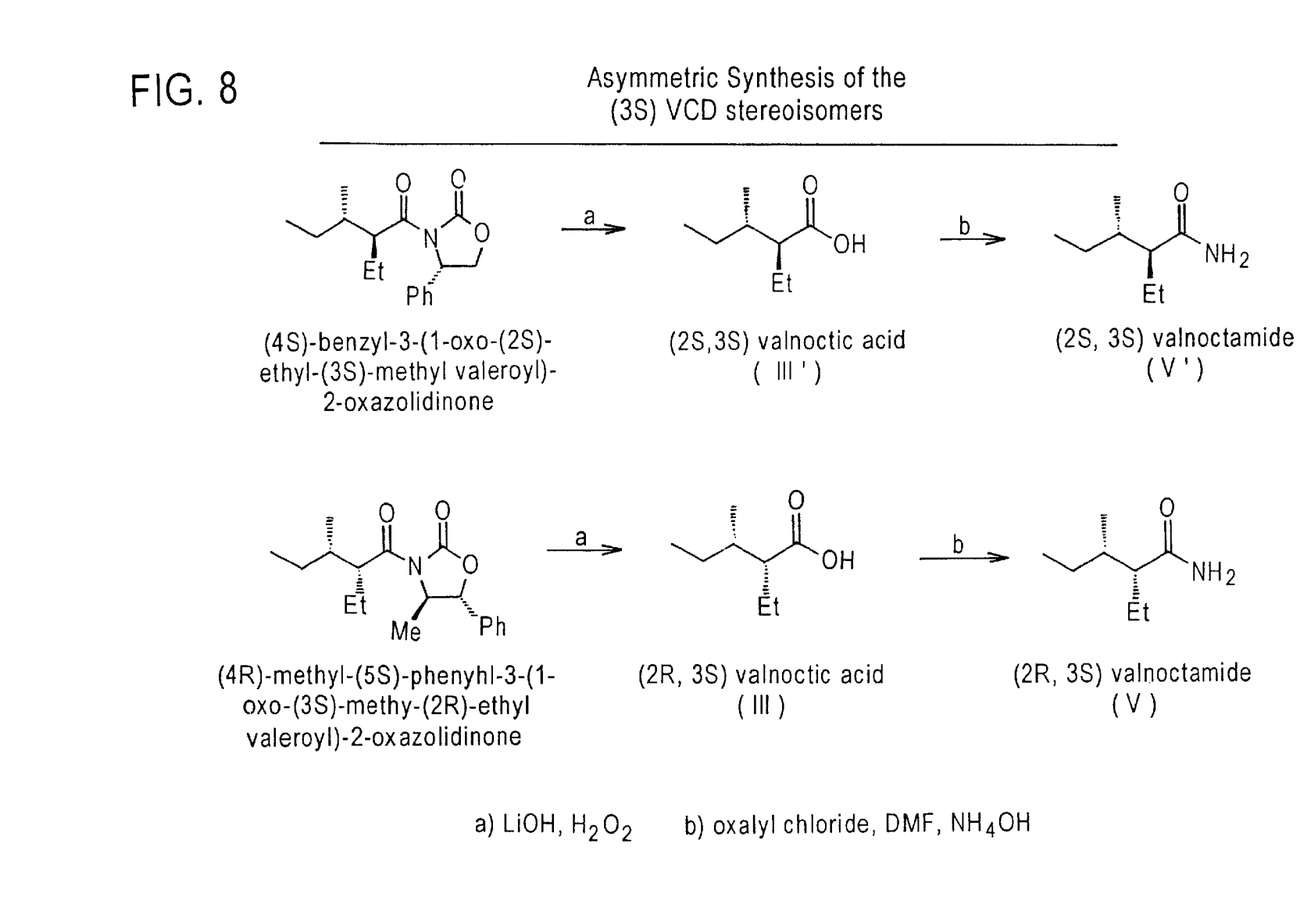

The present invention further relates to a method for the stereoselective synthesis of the valnoctamide stereoisomers (2S,3S) and (2R,3S). The said method of synthesis comprises the following steps;

(a) synthesizing (3S)-methyl valeric acid (see FIG. 6(I)) from L-isoleucine;

(b) synthesizing of (3S)-methyl valeroyl chloride (see FIG. 7(II));

(c) synthesizing (2S,3S) valnoctic acid (see FIG. 8(III')) or subsequently synthesizing (2R,3S) valnoctic acid (see FIG. 8(III));

(d) synthesizing (2S,3S) valnoctamide (see FIG. 8(V')) or (2R,3S) valnoctamide (see FIG. 8(V)). The said invention will be further illustrated by the following experiments. These experiments do not intend to limit the scope of the invention, but to demonstrate and clarify it only. The method of separation of the present invention was applied to investigate the pharmacokinetics of VCD stereoisomers in plasma samples from seven healthy subjects and six epileptic patients.

Healthy Subjects Seven healthy male volunteers, aged 20–31 years, weighing 61 to 85 kg, received 2×200 mg valnoctamide tablets (Nirvanil@) at 08:00 hours after an overnight fast. Venous blood samples were taken through an indwelling catheter 0, 0.5, 1, 2, 3, 4, 5, 6, 8, 10, 12 and 24 hours after dosing. Food was witheld for 4 hours after dosing.

Patients Six epileptic patients (four men and two women aged 23–35 years, with a body weight of 56–85 kg) were studied. All had been receiving a constant carbamazepine dose (800–1200 mg/day) for at least three months. One patient was also receiving phenytoin (250 mg/day) and a second patient phenobarbital (150 mg/day). Each patient received add-on VCD for eight consecutive days at a dosage of 400 mg on day 1 (single dose day), followed by 200 mg three times daily (tid) for seven days. On the last day, only the morning and the midday doses were administered. Blood samples for plasma VCD levels were collected at 0, 0.25, 0.5, 1, 1.5, 2, 3, 4, 5, 6, 8, 10, 12 and 24 hours after the first and the last morning dose. Additional samples were taken at times 0, 0.5, 1, and 2 hours after the morning dose on the last treatment day.

Figure 2A:
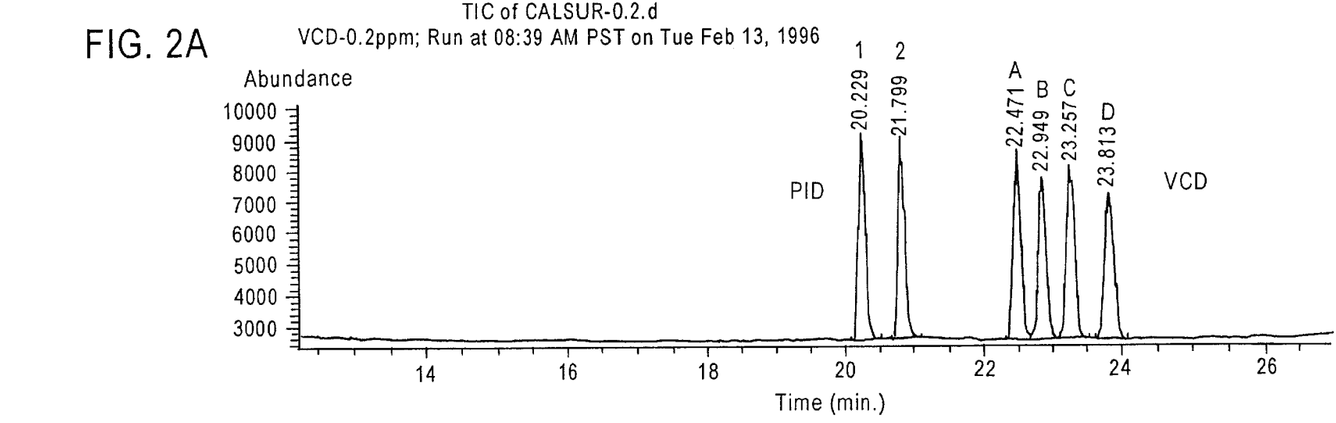
Figure 2B:
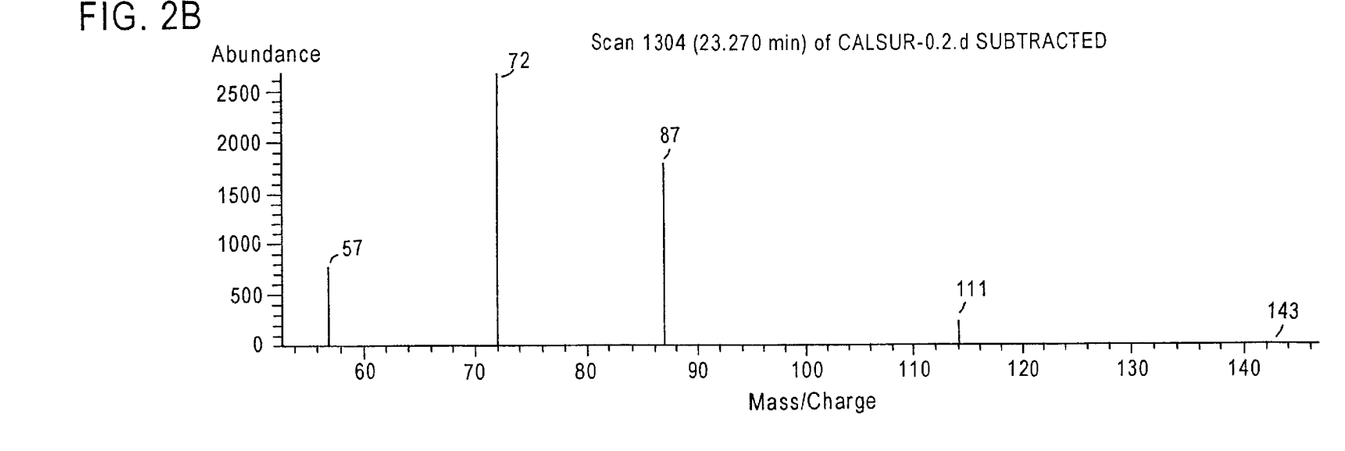

Plasma Handling and Analytical Assays Plasma samples were separated immediately by centrifugation at 2,000 g for 10 minutes and stored at −20° C. until assaying (VCD is stable at −20° C.). The VCD plasma samples were analyzed by a gas chromatograph (HP 5890 series II)-mass spectrometer (HP 5989A)-GC-MS data system equipped with chiral capillary column. The mass spectrometer was operated in E1 mode at 70eV, the source temperature of the MS was maintained at 200° C. and the quadruple at 100° C. Mass units and their relative abundance were calibrated with perfluorotributylamine (PFTBA). Spectra were collected in the range of 35 to 350 MHz, and the chiral analysis started 18 minutes after injection. Gas chromatograph (GC) oven temperature programming conditions were as follows: 50° C. for 1 minute, then increasing at a rate of 8° C./minute until 100° C., holding for a minute then 4° C./minute until reaching a final temperature of 250° C. The injector temperature is 240° C. and the GC-MS transfer line temperature is 250° C. Inlet pressure is 5 psi with a linear flow rate 20 cm/second. Helium was used as the carrier gas. Chromatographic resolution of the VCD stereoisomers was accomplished by a direct separation on a chiral stationary phase (CSP) column. The CSP consisted of a Chirasil-γ-Dex (octakis (3-O-butanoyl-2,6-di-o-pentyl)-γ-cyclodextrin chemically linked via a 6-mono-octamethylene spacer to a dimethylpolysiloxane. The 0.25 μm Chirasil-γ-Dex was coated on a 25 m×250 μm (id) fused silica capillary column. This CSP of a cyclodextin derivative allows complete baseline resolution of the four stereoisomers (α=1.04, Rs=2.0–2.4) in 24 minutes as depicted in FIG. 2. Intra and inter-day variability in the retention times of the four VCD stereoisomers was less than 10%. A calibration curve was established by spiking drug-free plasma samples with known amounts of racemic VCD at a concentration range of 0.2 mg/L to 8 mg/L (or 0.05 mg/L to 2 mg/L of each of the four VCD stereoisomers).

Reagents and Materials VCD (racemic mixture) was obtained from Clin Midy (Italy). Propylisopropylacetamide (PID), previously synthesized by Haj-Yehia and Bialer (Pharm Res 6:683–9,1989), was used as internal standard (IS). Stock solution of VCD (racemic mixture) was prepared by dissolving the drug in chloroform at a concentration of 5 mg/mL. The internal standard (PID) was dissolved in chloroform at a concentration of 10 mg/mL. The stock solutions were stored at −20° C.

Pharmacokinetic and Statistical Analysis Pharmacokinetic parameters were calculated by noncompartmental analysis according to statistical moment theory. Peak plasma concentrations (Cmax) and peak times (tmax) were derived directly from the measured values. The linear terminal slopes ($\lambda$) of the log-concentration of each VCD stereoisomer versus time curves were calculated by the peeling procedure. Half life ($t_{1/2}$) values were calculated as $0.693/\lambda$. Areas under the plasma concentration versus time curve (AUC), after single dosing, were calculated by the trapezoidal rule with extrapolation to infinity by dividing the last measured concentration by the terminal slope. During repeated administration AUC was calculated over the last two dosing intervals by using the trapezoidal rule. Mean residence time (MRT) was calculated after single dosing as AUMC/AUC, in which AUMC is the area under the concentration×time product versus time curve from zero to infinity. Following single dosing, oral clearance (CL/F, in which F is the oral availability) and apparent volume of distribution at steady state (Vss/F) were calculated as Dose/AUC and as MRT×CL/F, respectively. Following repeated dosing, CL/F was calculated from the quotient of the dose (200 mg) and the AUC obtained during one dosing interval (defined as one-half of the AUC calculated over two consecutive dosing intervals). Comparison of the pharmacokinetic parameters of all four VCD stereoisomers was made by ANOVA.

Figure 3:
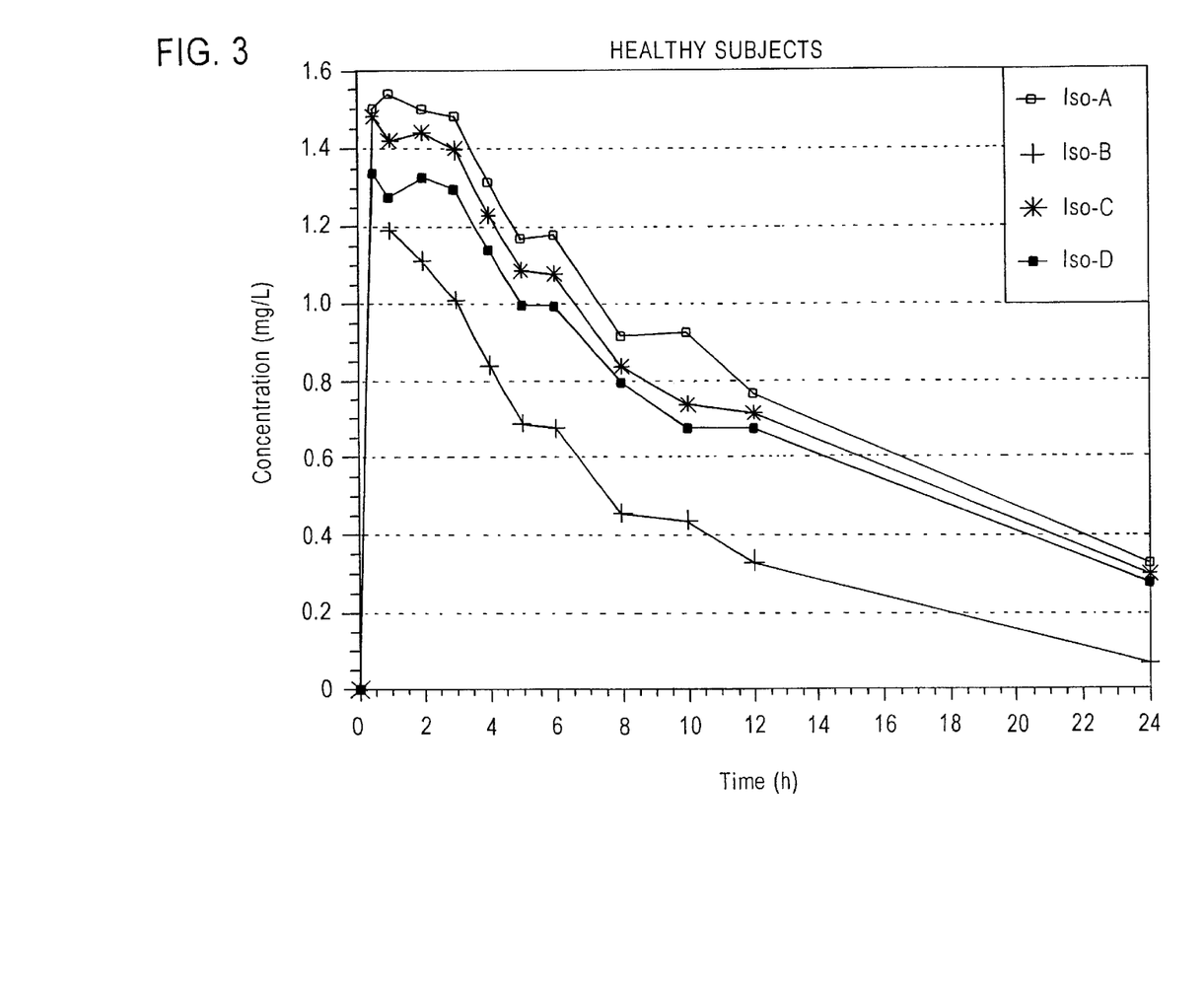
Figure 4:
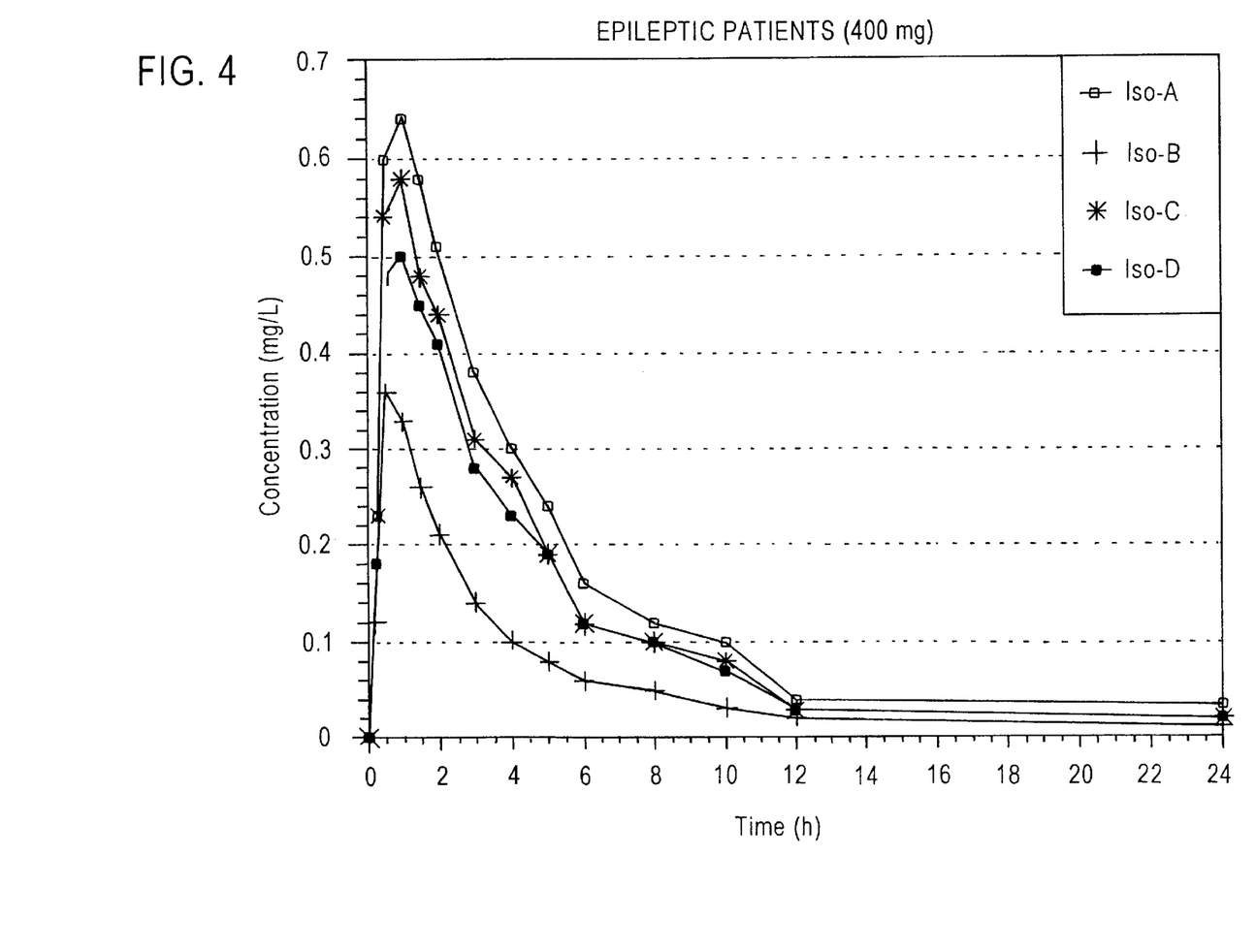
Figure 5:
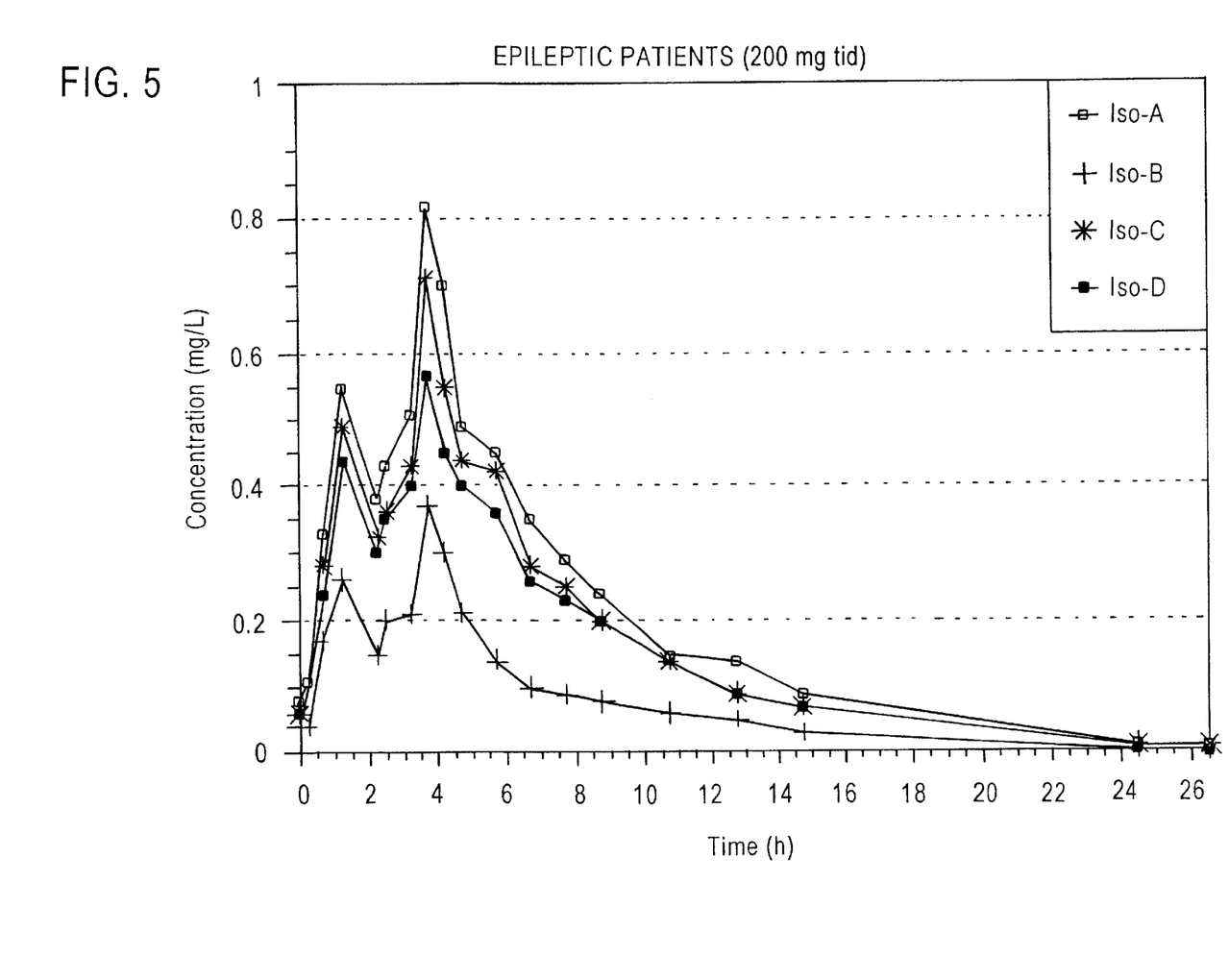

Results The stereoisomers of VCD were identified as A, B, C and D based on their respective retention times as shown in FIG. 1. As a step towards characterization, enantiomeric pairs of diastereisomers were separated by repeated crystallization of racemic VCD. After eight re crystallizations, a fraction of one pair of enantiomers (A and C) contained only 12% of the other enantiomeric pair (B and D). Intra-day and inter-day coefficients of variation for each analyte were below 10%. FIG. 2 shows a typical GC-MS chromatogram depicting the high resolution of the four stereoisomers (peaks A, B, C, and D) of VCD. The mass spectrum of each of the four VCD stereoisomers was identical. The mean plasma concentrations of the four stereoisomers following single oral dosing of racemic VCD to healthy subjects and epileptic patients are shown in FIGS. 3 and 4, while FIG. 5 depicts the mean plasma concentrations of the stereoisomers during the last day after eight days of repeated oral dosing of racemic VCD in epileptic patients. FIG. 5 exhibits primary and secondary peaks due to the fact that on the last day only 2 hours elapsed between the morning and the midday doses. The individual and mean pharmacokinetic parameters of the stereoisomers in healthy subjects and epileptic patients are given in Tables 1 to 3. In healthy subjects stereoisomer B had the largest oral clearance (CL/F=8.7+_ 0.9 L/h) and its half-life ($t_{1/2}$) and mean residence time (MRT) were the shortest of all VCD stereoisomers. Following single doses of VCD in epileptic patients, stereoisomer B also showed the largest oral clearance (80+_20L/h) and the largest volume of distribution (Vss/F=349+_60 L) compared to all the other stereoisomers. For all stereoisomers, CL/F values in epileptic patients were about 10-fold greater than those determined in healthy subjects who received the same dose under identical conditions. Vss/F values were also much larger in patients than in healthy subjects. Because of their short half-lives, all stereoisomers showed negligible accumulation during repeated dosing (FIG. 5 and Table 3). After 7-day dosing, however, CL/F values at steady-state were lower than those determined in the same patients after a single dose.

Figure 9:
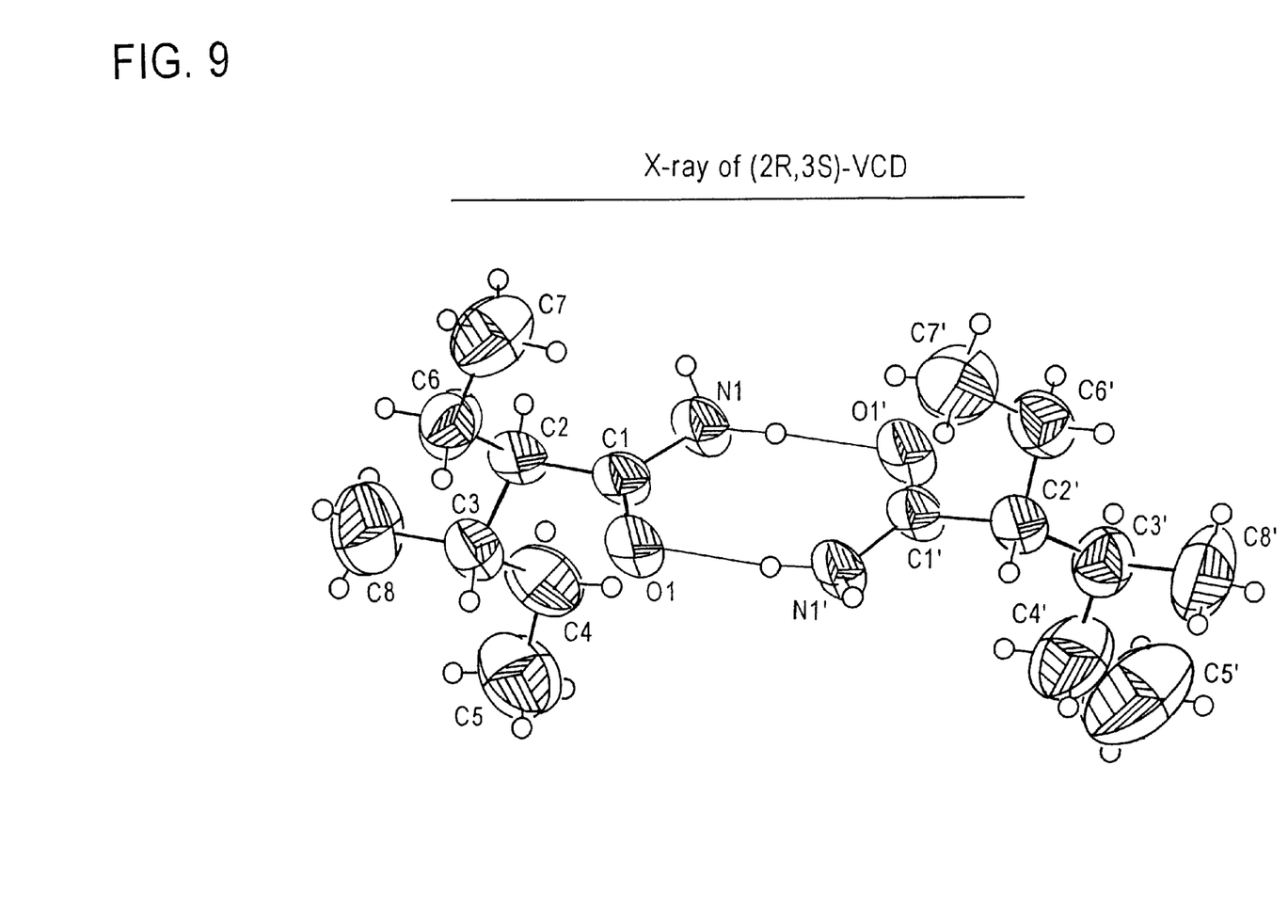

This study provides the first PK characterization of the four stereoisomers of VCD in man. When the concentration of individual isomers in plasma was added up at each sampling time, the resulting values were in close agreement with those determined previously in the same samples by using a different non-stereoselective GC assay (Pisani et al., Epilepsia 34:954–959, 1993). This provides confirmatory evidence for the reliability of the assay used in this study and for the stability of VCD under the indicated storage conditions. Evaluation of the kinetic properties of individual isomers in healthy subjects and in epileptic patients receiving concomitant anticonvulsant therapy clearly demonstrated that VCD pharmacokinetics is stereoselective, with one isomer (stereoisomer B) exhibiting a much higher clearance and a shorter half-life compared to other isomers. In fact, a pronounced difference in PK behavior was observed not only between stereoisomer B and its diastereoisomers A and C, but also between individual enantiomers B and D. Previous studies have shown that VCD is completely absorbed and is eliminated predominantly by metabolism. Therefore, the difference in PK properties between individual stereoisomers must involve a stereoselective process in the metabolism of the drug. In this respect, the larger apparent volume of distribution (Vss/F) of stereoisomers B, which was most clearly evident in epileptic patients, could be related to higher first-pass metabolism of this isomer, resulting in reduced oral bioavailability. Compared with healthy control subjects, epileptic patients exhibited an approximately 10-fold greater apparent oral clearance (CL/F) for each of the four stereoisomers. Epileptic patients also showed shorter half lives compared with control (about 3 h vs. 10 h for stereoisomers A,C and D, and about 3 h vs. 5.8 h for stereoisomer B). The prominent VCD elimination between healthy subjects and epileptic patients could be explained by induction of the oxidative metabolism of VCD stereoisomers by carbamazepine which is a potent inducer of cytochrome P450. Indeed the minimal urinary excretion of unchanged VCD and its minor metabolic hydrolysis to its corresponding acid VCA suggest that oxidative metabolic pathways play an important role in VCD elimination. Induction of first-pass metabolism by carbamazepine may also explain the larger volumes of distribution (Vss/F) of VCD stereoisomers in patients with epilepsy. The decrease in apparent oral clearance of VCD isomers which was observed during repeated dosing in epileptic patients, on the other hand, is suggestive of time-dependent changes in VCD disposition, possibly related to concentration-dependent metabolism of the drug. Although stereoselective pharmacodynamics is not necessarily associated with PK stereoselectivity, the differences in PK behavior of VCD stereoisomers increase the likelihood that differences also exist in their anticonvulsant activity or undesired properties such as teratogenicity, hepatotoxicity and epoxide hydrolase inhibition. A unique method for the synthesis of individual stereoisomer was developed and their absolute configuration was resolved by X-RAY diffraction analysis as shown in FIG. 9.

The method for the asymetric synthesis of the 2S, 3S and 2R,3S VCD stereoisomers will be further described by the following examples:.

Synthetic procedure of (2S,3S)-valnoctamide 1. (2S 3S)-2-bromo-3-methyl valeric acid To a cooled (0° C.) solution of L-Isoleucine (66 g) dissolved in HBr (6N, 500 ml) was added dropwise a solution of sodium nitrite (35 g in 100 ml water). The reaction was stirred overnight at room temperature and then extracted with EtOAc (3×150 ml). The combined organic extracts washed with 10% sodium bisulfit solution, water, saturated brine, dried over $MgSO_4$, filtered and concentrated. The product a yellowish oil (53.9 g) was obtained in 55% yield. (The product can be purified by distillation and crystallization from PE). (see FIG. 6)

2. (3S)-methyl valeric acid

To a solution of (3S)-methyl valeric acid (53.9 g) dissolved in sulfuric acid (1N, 800 ml) was added slowly zinc powder (36 g). The reaction was stirred for two hours, filtered and extracted with $Et_2O$ (3×200 ml). The combined organic extracts washed with water, saturated brine, dried over $MgSO_4$ and concentrated. The Yellowish oil obtained was purified by distillation under reduced pressure (5 torr, bp=55° C.). The product a colorless oil (18.5 g) was obtained in 58% yield. (see FIG. 6).

3. (2S,3S)-2-chloro-3-methyl valeric acid

To a cooled (0° C.) solution of L-Isoleucine (40 g) dissolved in HCl (5N, 750 ml) was added dropwise a solution of sodium nitrite (35 g in 100 ml water). The reaction was stirred overnight at room temperature (~23° C.), $Na_2CO_3$ (31 g) slowly added and the reaction mixture extracted with EtOAc (3×150 ml). The combined organic extracts washed with water, half saturated brine, dried over $MgSO_4$, filtered and concentrated. The product a yellowish oil was distilled under reduced pressure (5 torr, bp=111° C.) to afford a colorless oil (32 g) obtained in 70% yield. (see FIG. 6).

4. (3S)-methyl pentanol

To a solution of (2S,3S)-2-chloro-3-methyl valeric acid (66 g) dissolved in 2500 ml of dry $Et_2O$ was carefully added powdered LAH (50 g). The reaction was refluxed for 7–10 days. Excess LAH was neutralized by careful addition of EtAOc (250 ml), methanol (100 ml), DDW (100 ml) and a 1:1 sulfuric acid and water mixture (100 ml). The etheral phase separated and the aqueous phase extracted with EtOAc (3×200 ml). The combined organic extracts washed with a 10% $NaHCO_3$ solution, water, half saturated brine, dried over $MgSO_4$ and concentrated. The product, a green oil, was purified by vacuum distillation (5 torr, bp=42° C.) to afford a colorless oil (27.3 g), 61% yield. (see FIG. 6).

5. (3S)-methyl valeric acid

To a cool (0° C.) solution of (3S)-methyl pentanol (37.9 g) dissolved in 1500 ml $Et_2O$ was slowly added 1200 ml of the oxidation reagent (240 g $Na_2Cr_2O_7$, 177 ml $H_2SO_4$ 97% and DDW to make 1200 ml). The reaction was stirred overnight at room temperature (~23° C.) and extracted with $Et_2O$ (3×150 ml). The combined organic extracts washed with 5% HCl solution (3×50 ml) followed by alkalization with 2N NaOH solution. The alkaline aqueous phase separated, acidified with concentrated HCl (PH=2) and extracted with EtOAc (3×100 ml). The combined organic extracts dried over $MgSO_4$ and concentrated to give a dark oil which was purified by vacuum distillation (5 torr, bp=110° C.) to afford a colorless oil (25.2 g), 58% yield. (see FIG. 6).

6. (3S)-methyl valeryol chloride

To a cooled (0° C.) solution of (3S)-methyl valeric acid (10 g) and dry DMF (6.7 ml) dissolved in dry DCM (50 ml) was added dropwise oxalyl chloride (7.3 ml in 50 ml dry DCM). After sing one hour the DCM and excess oxalyl chloride were evaporated by $N_2$ stream. The crude product was rinsed with dry DCM (2×20 ml) which was evaporated by $N_2$ stream. The reaction mixture was dissolved in cooled (0° C.) dry THF (20 ml) and used without further purification at the next step. (see FIG. 7).

7. (4S,3'S)-3-(3'-methyl-1'-oxopentyl)-4-benzyl-2-oxazolidinone

To a cooled (−78° C.) solution of (4S)-benzyl-2-oxazolidinone (3.65 g) dissolved in dry THF (50 ml) was added dropwise a solution of n-BuLi (13 ml, 1.6 M in hexane). After stirring for 30 min a cooled (−78° C.) solution of (3S)-methyl valeryol chloride (~2.8 g) dissolved in dry THF (20 ml) was added via cannula at once. The reaction mixture was slowly warmed to 0° C., stirred for 2 hours and quenched by addition of saturated $NH_4Cl$ solution. The THF evaporated and the aqueous phase extracted with DCM (3×50 ml). The combined organic extracts washed with water, half saturated brine, dried over $MgSO_4$ and concentrated. The product (3.9 g) was crystallized from 5% EtOAc in PE, yield 690%. (see FIG. 7).

8. (4S,2'S,3'S)-3-(2'-ethyl-3'-methyl-1'-oxopentyl)-4-benzyl-2-oxazolidinone

Synthesis by the same procedure as (4S,2'R)-3-(2'-isopropyl-1'-oxopentyl)-4-benzyl-2-oxazolidinone using (4S,3'S)-3-(3'-methyl-1'-oxopentyl)-4-benzyl-2-oxazolidinone and ethyl trifluoromethane sulphonate. (see FIG. 7).

9. (2S,3S)-valnoctic acid ((2S,3S)-VCA)

(4R,5S,2'S)-3-(2'-isopropyl-1'-oxopentyl)-4methyl-5-phenyl-2-oxazolidinone was synthesized from (4R,5S)-3-(1'-oxopentyl)-4methyl-5-phenyl-2oxazolidinone and isopropyl triflate by the same procedure as (4S,2'S)-3-(2'-isopropyl-1'-oxopentyl)-4-benzyl-2-oxazolidinone. The product (5.53 g) was obtained in 32% yield. (see FIG. 8).

10. (2S,3S)-valnoctamide ((2S,3S)-VCD)

Under $N_2$ to a cooled (0° C.) solution of (2R)-PIA (3.3 g) dissolved in dry DCM (100 ml) and dry DMF (1.77 ml) was added dropwise a solution of oxalyl chloride (34.3 ml, 2.0 M solution in DCM). After stirring one hour the DCM and excess oxalyl chloride were evaporated by $N_2$ stream. In order to remove traces of oxalyl chloride the crude product was treated with dry DCM (2×20 ml) which was evaporated by $N_2$ stream. To the crude reaction mixture dissolved in cooled (0° C.) dry DCM (100 ml) was added $NH_4OH$ (20 ml, 25% solution in water) and the reaction mixture stirred for an hour. The organic phase washed with water and half saturated brine, dried over $MgSO_4$, filtered and concentrated. The product was crystallized from 20% EtOAc in PE to afford 2.14 g, 65% yield.

Synthetic procedure of (2R,3S)-valnoctamide

Synthesis of (2R,3S)-VCD is performed by using the same procedures as for the synthesis of (2S,3S)-VCD except for the chiral auxiliary which is (4R,5S)4-methyl-5-phenyl-2-oxazolidinone.

TABLE I

Pharmacokinetic parameters of the stereoisomers of vainoctamide (VCD) following single oral administration (400 mg) of the commercially available racemic drug (Nivanil) to seven healthy subjects.

| | Subjects | | | | | | | |
|---|---|---|---|---|---|---|---|---|
| | CP | CG | ML | GM | VL | BV | GL | Mean ± SD |
| Stereoisomer A | | | | | | | | |
| t½ (h) | 8.8 | 13.6 | 8.1 | 10.7 | 9.5 | 8.5 | 12.5 | 10.2 ± 2.1 |
| Cmax (mg/L) | 2.0 | 1.5 | 1.8 | 1.8 | 1.7 | 1.8 | 1.5 | 1.7 ± 0.2 |
| tmax (h) | 1 | 0.5 | 1 | 1 | 0.5 | 0.5 | 0.5 | 0.7 ± 0.3 |
| CL/F (L/h) | 3.6 | 4.5 | 4.1 | 3.7 | 4.6 | 4.2 | 3.5 | 4.2 ± 0.6 |
| Vss/F (L) | 46 | 89 | 48 | 55 | 62 | 52 | 63 | 59 ± 15 |
| MRT (h) | 13 | 20 | 12 | 15 | 13 | 12 | 18 | 15 ± 3 |
| Stereoisomer B | | | | | | | | |
| t½ (h) | 4.7 | 7.3 | 4.6 | 6.0 | 5.8 | 5.2 | 7.1 | 5.8 ± 1.1* |
| Cmax (mg/L) | 1.5 | 1.1 | 1.4 | 1.4 | 1.4 | 1.5 | 1.1 | 1.3 ± 0.2 |
| tmax (h) | 1 | 0.5 | 1 | 1 | 0.5 | 0.5 | 0.5 | 0.7 ± 0.3 |
| CL/F (L/h) | 7.9 | 9.2 | 7.9 | 8.4 | 10.2 | 8.1 | 9.3 | 8.7 ± 0.9* |
| Vss/F (L) | 57 | 94 | 58 | 73 | 83 | 62 | 91 | 74 ± 16 |
| MRT (h) | 7.0 | 10 | 7 | 9 | 8 | 8 | 10 | 8 ± 1 |
| Stereoisomer C | | | | | | | | |
| t½ (h) | 8.4 | 13 | 8.0 | 10 | 11.1 | 9.2 | 12.4 | 10.3 ± 1.9 |
| Cmax (mg/L) | 1.8 | 1.4 | 1.7 | 1.7 | 1.6 | 1.8 | 1.5 | 1.6 ± 0.2 |
| tmax (h) | 1 | 0.5 | 1 | 1 | 0.5 | 0.5 | 0.5 | 0.7 ± 0.3 |
| CL/F (L/h) | 4.0 | 5.1 | 4.3 | 4.1 | 4.6 | 4.1 | 3.9 | 4.3 ± 0.4 |
| Vss/F (L) | 49 | 93 | 50 | 58 | 72 | 55 | 70 | 64 ± 16 |
| MRT (h) | 12 | 18 | 12 | 14 | 16 | 13 | 18 | 15 ± 3 |
| Stereoisomer D | | | | | | | | |
| t½ (h) | 8.7 | 12.9 | 8.0 | 13.0 | 9.5 | 7.9 | 13 | 10 ± 2 |
| Cmax (mg/L) | 1.5 | 1.3 | 1.6 | 1.5 | 1.4 | 1.8 | 1.5 | 1.5 ± 0.2 |
| tmax (h) | 1 | 0.5 | 1 | 1 | 0.5 | 0.5 | 0.5 | 0.7 ± 0.3 |
| CL/F (L/h) | 4.3 | 5.6 | 4.8 | 3.8 | 5.4 | 4.7 | 4.1 | 4.6 ± 0.7 |
| Vss/F (L) | 54 | 102 | 53 | 70 | 72 | 55 | 76 | 69 ± 17 |
| MRT (h) | 13 | 18 | 12 | 18 | 13 | 12 | 19 | 15 ± 3 |

(*p < 0.05 vs. stereoisomers A, C and D)

TABLE II

Pharmacokinetic parameters of the stereoisomers of vainoctamide (VCD) following single oral administration (400 mg) of the commercially available racemic VCD (Nirvanil) to six epileptic patients.

| | Patients | | | | | | | |
|---|---|---|---|---|---|---|---|---|
| | CA | CC | ML | DFR | PA | SG | CCA | Mean ± SD |
| Stereoisomer A | | | | | | | | |
| t½ (h) | 2.8 | 3.6 | | 2.5 | 3.6 | 8.3 | 3.8 | 4.1 ± 2.1 |
| Cmax (mg/L) | 0.71 | 0.94 | | 0.71 | 0.82 | 0.88 | 0.67 | 0.78 ± 0.10 |
| tmax (h) | 1.5 | 0.5 | | 1.5 | 0.5 | 0.5 | 0.5 | 0.8 ± 0.5 |
| CL/F (L/h) | 40 | 27 | | 35 | 32 | 20 | 35 | 32 ± 7 |
| Vss/F (L) | 175 | 138 | | 148 | 172 | 169 | 182 | 164 ± 17 |
| MRT (h) | 4.4 | 5.1 | | 4.3 | 5.3 | 8.3 | 5.1 | 5.4 ± 1.5 |
| Stereoisomer B | | | | | | | | |
| t½ (h) | 1.4 | 4.0 | | 1.3 | 3.0 | 4.0 | 4.1 | 3.0 ± 1.3 |
| Cmax (mg/L) | 0.31 | 0.56 | | 0.3 | 0.48 | 0.51 | 0.32 | 0.41 ± 0.12 |
| tmax (h) | 1 | 0.5 | | 1.5 | 0.5 | 0.5 | 0.5 | 0.75 ± 0.41 |
| CL/F (L/h) | 108 | 60 | | 94 | 84 | 56 | 79 | 80 ± 20* |
| Vss/F (L) | 386 | 307 | | 307 | 365 | 287 | 444 | 349 ± 50* |
| MRT (h) | 3.6 | 5.2 | | 3.3 | 1.3 | 5.1 | 5.6 | 4.0 ± 1.6 |
| Stereoisomer C | | | | | | | | |
| t½ (h) | 2.8 | 3.4 | 2.6 | | 3.7 | 3.5 | 3.7 | 3.3 ± 0.5 |
| Cmax (mg/L) | 0.55 | 0.82 | 0.56 | | 0.76 | 0.8 | 0.7 | 0.7 ± 0.12 |
| tmax (h) | 1.5 | 0.5 | 1.5 | | 0.5 | 0.5 | 0.5 | 0.83 ± 0.5 |
| CL/F (L/h) | 50 | 31 | 44 | | 38 | 28 | 41 | 39 ± 8 |
| Vss/F (L) | 215 | 147 | 186 | | 208 | 141 | 197 | 181 ± 31 |
| MRT (h) | 4.4 | 4.8 | 4.2 | | 5.4 | 5.0 | 4.8 | 4.8 ± 0.4 |

TABLE II-continued

Pharmacokinetic parameters of the stereoisomers of vainoctamide (VCD) following single oral administration (400 mg) of the commercially available racemic VCD (Nirvanil) to six epileptic patients.

| | Patients | | | | | | | |
|---|---|---|---|---|---|---|---|---|
| | CA | CC | ML | DFR | PA | SG | CCA | Mean ± SD |
| Stereoisomer D | | | | | | | | |
| t½ (h) | 1.2 | 3.8 | | 2.7 | 3.8 | 3.9 | 3.8 | 3.3 ± 1.1 |
| Cmax (mg/L) | 0.51 | 0.72 | | 0.51 | 0.69 | 0.72 | 0.51 | 0.61 ± 0.11 |
| tmax (h) | 1.5 | 0.5 | | 1.5 | 0.5 | 0.5 | 0.5 | 0.83 ± 0.51 |
| CL/F (L/h) | 60 | 35 | | 45 | 42 | 30 | 42 | 46 ± 11 |
| Vss/F (L) | 195 | 183 | | 198 | 233 | 161 | 226 | 202 ± 22 |
| MRT (h) | 3.3 | 5.2 | | 4.5 | 5.6 | 5.4 | 5.3 | 4.7 ± 1.0 | available racemic VCD (Nirvanil) to six epileptic patients during the last dosing interval and the last day of the study.

| Stereoisomer A | | | | | | | | |
|---|---|---|---|---|---|---|---|---|
| t½ (h) | 2.2 | 2.7 | | 3.8 | 2.4 | 4.8 | 3.8 | 2.8 ± 0.7 |
| Cmax (mg/L) | 0.9 | 1.1 | | 0.72 | 0.86 | 0.8 | 1.2 | 0.9 ± 0.2 |
| tmax (h) | 2.0 | 1.5 | | 1.5 | 1.0 | 1.75 | 1.5 | 1.5 ± 0.3 |
| CL/F (L/h) | 23 | 19 | | 20 | 29 | 19 | 19 | 21 ± 4 |
| Stereoisomer B | | | | | | | | |
| t½ (h) | 2.0 | 1.9 | | 2.9 | 2.1 | 4.3 | 4.3 | 2.2 ± 0.5 |
| Cmax (mg/L) | 0.4 | 0.5 | | 0.3 | 0.3 | 0.4 | 0.5 | 0.4 ± 0.1 |
| tmax (h) | 2.0 | 1.5 | | 1.5 | 1.0 | 1.25 | 1.5 | 1.4 ± 0.3 |
| CL/F (L/h) | 79 | 50 | | 52 | 71 | 46 | 50 | 58 ± 14* |
| Stereoisomer C | | | | | | | | |
| t½ (h) | 2.2 | 3.0 | | 4.1 | 2.3 | 5.0 | 4.1 | 2.9 ± 0.9 |
| Cmax (mg/L) | 0.81 | 0.9 | | 0.62 | 0.7 | 0.6 | 1.0 | 0.8 ± 0.2 |
| tmax (h) | 2.0 | 1.5 | | 1.5 | 1.0 | 1.25 | 1.5 | 1.4 ± 0.3 |
| CL/F (L/h) | 26 | 23 | | 24 | 36 | 28 | 23 | 27 ± 5 |
| Stereoisomer D | | | | | | | | |
| t½ (h) | 2.1 | 2.8 | | 5.2 | 2.5 | 5.3 | 4.6 | 3.2 ± 1.4 |
| Cmax (mg/L) | 0.7 | 0.8 | | 0.6 | 0.6 | 0.6 | 0.5 | 0.6 ± 0.1 |
| tmax (h) | 2.0 | 1.5 | | 1.5 | 1.0 | 1.25 | 1.5 | 1.4 ± 0.3 |
| CL/F (L/h) | 36 | 25 | | 25 | 38 | 24 | 25 | 29 ± 6 |

(*p < 0.05 vs. stereoisomers A, C and D)

What is claimed is:

1. A method for the stereoselective synthesis of the valnoctamide stereoisomers (2S,3S) and (2R,3S) comprising;
   (a) synthesizing (3S)-methyl valeric acid (I) from L-isoleucine;
   (b) subsequently synthesizing (3S)-methyl valeroyl chloride (II) from said (3S)-methyl valeric acid (I);
   (c) subsequently synthesizing (2S),(3S) valnoctic acid (III'), or subsequently synthesizing (2R),(3S) valnoctic acid (III), from said (3S) methyl valeroyl chloride; and
   (d) subsequently synthesizing (2S),(3S) valnoctamide (V'), or (2R),(3S) valnoctamide (V), from said (2S),(3S) valnoctic acid (III'), or said (2R),(3S) valnoctic acid (III), respectively.

2. A pharmaceutical composition containing an active ingredient consisting essentially of at least one stereoisomer of valnoctamide selected from the group consisting of the (2R),(3S) isomer and the (2S),(3S) isomer, wherein said selected isomer has been made according to claim 1.

3. A pharmaceutical composition according to claim 2 having the property of ameliorating convulsant behavior.

4. A method for baseline separation of the four valnoctamide stereoisomers comprising subjecting a racemic mixture of valnoctamide stereoisomers to gas chromatography followed by separating the stereoisomers on a chiral stationary phase column.

5. A method according to claim 4 wherein the gas chromatography (GC) has oven temperature programming conditions of: 50° C. for 1 minute, increasing the temperature at a rate of 8° C./minute until 100° C., holding for a minute at 100° C., then increasing the temperature at a rate of 4° C./minute to reach a final temperature of 250° C.; injecting a sample at a temperature of 240° C. and maintaining the GC-MS transfer line temperature at 250° C.; an inlet pressure of 5 psi with a linear flow rate 20 cm/second, and the GC carrier gas is helium.

6. A method according to claim 4 wherein the chiral stationary phase column comprises octakis (3-O-butanoyl-2,6-di-o-pentyl)-γ-cyclodextrin chemically linked, via a 6-mono-octamethylene spacer, to a dimethylpolysiloxane that is coated on a fused silica capillary column.

7. A method of treating a neurological disorder in a patient which comprises administering an effective amount of at least one stereoisomer of valnoctamide selected from the group consisting of the (2R),(3S) stereoisomer, and the (2S),(3S) stereoisomer to said patient for a time sufficient to ameliorate the effects of said neurological disorder.

8. A method of treating a psychotic disorder in a patient which comprises administering an effective amount of at least one stereoisomer of valnocamide selected from the group consisting of the (2R),(3S) stereoisomer and the (2S),(3S) stereoisomer to said patient for a time sufficient to ameliorate the effects of said psychotic disorder.

9. A method of treating an affective disorder, associated with a neurological disorder or a psychotic disorder, in a patient which comprises administering an effective amount of at least one stereoisomer of valnocamide selected from the group consisting of the (2S),(3S) sterodisomer and the (2R),(3S) stereoisomer to said patient for a time sufficient to ameliorate the effects of said neurological or psychotic disorder.

10. A method of tranquilizing a patient in need of tranquilization which comprises administering an effective amount of at least one stereoisomer of valnocamide selected from the group consisting of the (2S),(3S) stereoisomer and the (2R),(3S) stereoisomer to said patient.

11. A method of treating pain in a patient which comprises administering an effective amount of at least one stereoisomer of valnocamide selected from the group consisting of the (2S),(3S) stereoisomer and the (2R),(3S) stereoisomer to said patient for a time sufficient to ameliorate said pain.

12. A method of treating convulsions in a patient which comprises administering an effective amount of at least one stereoisomer of valnocamide selected from the group consisting of the (2S),(3S) stereoisomer and the (2R),(3S) stereoisomer to said patient for a time sufficient to ameliorate said convulsions.

13. A method of treating epilepsy in a patient which comprises administering an effective amount of at least one stereoisomer of valnocamide selected from the group consisting of the (2S),(3S) stereoisomer and the (2R),(3S) stereoisomer to said patient for a time sufficient to ameliorate said epilepsy.

14. A method as claimed in claim 7 wherein said stereoisomer of valnoctamide is made by a process comprising:
  (a) synthesizing (3S)-methyl valeric acid (I) from L-isoleucine;
  (b) subsequently synthesizing (3S)-methyl valeroyl chloride (II) from said (3S)-methyl valeric acid (I);
  (c) subsequently synthesizing (2S),(3S) valnoctic acid (III'), or subsequently synthesizing (2R),(3S) valnoctic acid (III), from said (3S) methyl valeroyl chloride; and
  (d) subsequently synthesizing (2S),(3S) valnoctamide (V'), or (2R),(3S) valnoctamide (V), from said (2S),(3S) valnoctic acid (III'), or said (2R),(3S) valnoctic acid (III), respectively.

15. A method as claimed in claim 9 wherein said stereoisomer of valnoctamide is made by a process comprising
  (a) synthesizing (3S)-methyl valeric acid (I) from L-isoleucine;
  (b) subsequently synthesizing (3S)-methyl valeroyl chloride (II) from said (3S)-methyl valeric acid (I);
  (c) subsequently synthesizing (2S),(3S) valnoctic acid (III'), or subsequently synthesizing (2R),(3S) valnoctic acid (III), from said (3S) methyl valeroyl chloride; and
  (d) subsequently synthesizing (2S),(3S) valnoctamide (V'), or (2R),(3S) valnoctamide (V), from said (2S),(3S) valnoctic acid (III'), or said (2R),(3S) valnoctic acid (III), respectively.

16. A method as claimed in claim 9 wherein said stereoisomer of valnoctamide is made by a process comprising
  (a) synthesizing (3S)-methyl valeric acid (I) from L-isoleucine;
  (b) subsequently synthesizing (3S)-methyl valeroyl chloride (II) from said (3S)-methyl valeric acid (I);
  (c) subsequently synthesizing (2S),(3S) valnoctic acid (III'), or subsequently synthesizing (2R),(3S) valnoctic acid (III), from said (3S) methyl valeroyl chloride; and
  (d) subsequently synthesizing (2S),(3S) valnoctamide (V'), or (2R),(3S) valnoctamide (V), from said (2S),(3S) valnoctic acid (III'), or said (2R),(3S) valnoctic acid (III), respectively.

17. A method as claimed in claim 8 wherein said stereoisomer of valnoctamide is made by a process comprising
  (a) synthesizing (3S)-methyl valeric acid (I) from L-isoleucine;
  (b) subsequently synthesizing (3S)-methyl valeroyl chloride (II) from said (3S)-methyl valeric acid (I);
  (c) subsequently synthesizing (2S),(3S) valnoctic acid (III'), or subsequently synthesizing (2R),(3S) valnoctic acid (III), from said (3S) methyl valeroyl chloride; and
  (d) subsequently synthesizing (2S),(3S) valnoctamide (V'), or (2R),(3S) valnoctamide (V) from said (2S),(3S) valnoctic acid (III'), or said (2R),(3S) valnoctic acid (III), respectively.

18. A method as claimed in claim 11 wherein said stereoisomer of valnoctamide is made by a process comprising
  (a) synthesizing (3S)-methyl valeric acid (I) from L-isoleucine;
  (b) subsequently synthesizing (3S)-methyl valeroyl chloride (II) from said (3S)-methyl valeric acid (I);
  (c) subsequently synthesizing (2S),(3S) valnoctic acid (III'), or subsequently synthesizing (2R),(3S) valnoctic acid (III), from said (3S) methyl valeroyl chloride; and
  (d) subsequently synthesizing (2S),(3S) valnoctamide (V'), or (2R),(3S) valnoctamide (V), from said (2S),(3S) valnoctic acid (III'), or said (2R),(3S) valnoctic acid (III), respectively.

19. A method as claimed in claim 12 wherein said stereoisomer, of valnoctamide is made by a process comprising
  (a) synthesizing (3S)-methyl valeric acid (I) from L-isoleucine;
  (b) subsequently synthesizing (3S)-methyl valeroyl chloride (II) from said (3S)-methyl valeric acid (I);
  (c) subsequently synthesizing (2S),(3S) valnoctic acid (III'), or subsequently synthesizing (2R),(3S) valnoctic acid (III), from said (3S) methyl valeroyl chloride; and
  (d) subsequently synthesizing (2S),(3S) valnoctamide (V'), or (2R),(3S) valnoctamide (V), from said (2S),(3S) valnoctic acid (III'), or said (2R),(3S) valnoctic acid (III), respectively.

20. A method as claimed in claim 13 wherein said stereoisomer of valnoctamide is made by a process comprising
  (a) synthesizing (3S)-methyl valeric acid (I) from L-isoleucine;
  (b) subsequently synthesizing (3S)-methyl valeroyl chloride (II) from said (3S)-methyl valeric acid (I);
  (c) subsequently synthesizing (2S),(3S) valnoctic acid (III'), or subsequently synthesizing (2R),(3S) valnoctic acid (III), from said (3S) methyl valeroyl chloride; and
  (d) subsequently synthesizing (2S),(3S) valnoctamide (V'), or (2R),(3S) valnoctamide (V), from said (2S),(3S) valnoctic acid (III'), or said (2R),(3S) valnoctic acid (III), respectively.

21. A method of making a (2S),(3S) stereoisomer of valnoctamide comprising:
   (a) synthesizing (3S)-methyl valeric acid (I) from L-isoleucinie;
   (b) subsequently synthesizing (3S)-methyl valeroyl chloride (II) from said (3S)-methyl valeric acid (I);
   (c) subsequently synthesizing (2S),(3S) valnoctic acid (III') from said (3S) methyl valeroyl chloride; and
   (d) subsequently synthesizing (2S),(3S) valnoctamide (V') from said (2S),(3S) valnoctic acid (III').

22. A method of making a (2R),(3S) stereoisomer of valnoctamide comprising:
   (a) synthesizing (3S)-methyl valeric acid (I) from L-isoleucine;
   (b) subsequently synthesizing (3S)-methyl valeroyl chloride (II) from said (3S)-methyl valeric acid (I);
   (c) subsequently synthesizing (2R),(3S) valnoctic acid (III) from said (3S) methyl valeroyl chloride; and
   (d) subsequently synthesizing (2R),(3S) valnoctamide (V) from said (2R),(3S) valnoctic acid (III).

23. A pharmaceutical composition containing a valnoctamide active ingredient, wherein said valnoctamide consists essentially of a (2R),(3S) stereoisomer of valnoctamide.

24. A pharmaceutical composition containing a valnoctamide active ingredient, wherein said valnoctamide consists essentially of a (2S),(3S) stereoisomer of valnoctamide.

* * * * *